United States Patent

Fujioka et al.

[11] Patent Number: 5,939,593
[45] Date of Patent: Aug. 17, 1999

[54] BROMINATED 1,3-DIMETHYL-3-PHENYL-1-(2-METHYL-2-PHENYLPROPYL)-INDANE AND METHOD FOR PREPARING THE SAME

[75] Inventors: Atsushi Fujioka; Kiyotaka Mashita; Takayuki Saito, all of Hitachi; Akihiro Kobayashi; Fumiaki Kanega, both of Ichihara, all of Japan

[73] Assignee: Hitachi Chemical Co., Ltd., Tokyo, Japan

[21] Appl. No.: 09/110,818

[22] Filed: Jul. 7, 1998

[30] Foreign Application Priority Data

Jul. 7, 1997 [JP] Japan ................................ 9-181451

[51] Int. Cl.$^6$ .................................................. C07C 22/00
[52] U.S. Cl. ............................................. 570/183; 570/206
[58] Field of Search ....................... 570/183, 206

[56] References Cited

FOREIGN PATENT DOCUMENTS 0 571 036  11/1993  European Pat. Off. .
6-122637   6/1994   Japan .

OTHER PUBLICATIONS

"Polybrominated Dibenzofurans and Dibenzo–p–dioxins: Thermal Reaction Products of Polybrominated Diphenyl Ether Flame Retardants", by Hans–Rudolf Buser (ES&T vol. 20 No. 4) Apr. 1986
Database WPI, Week 9703, Derwent Pub. Ltd., London, GB; AN 97–029559, XP002077445 & JP 08 291 241 A (Asahi Kasei Kogyo KK) Nov. 5 1996.

Primary Examiner—Alan Siegel
Attorney, Agent, or Firm—Fish & Richardson P.C.

[57] ABSTRACT

A brominated 1,3-dimethyl-3-phenyl-1-(2-methyl-2-phenylpropyl) indane herein disclosed is represented by the following general formula (I):

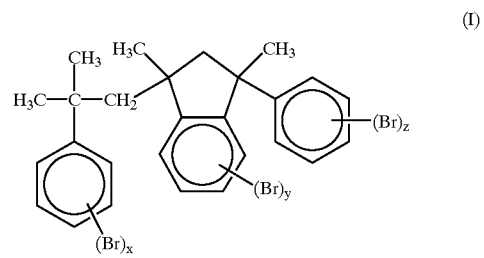

(wherein x and z each independently represents an integer ranging from 0 to 5, y represents an integer ranging from 0 to 4, provided that x+y+z>1). The compound can be prepared by a method which comprises the step of reacting 1,3-dimethyl-3-phenyl-1-(2-methyl-2-phenylpropyl) indane with a bromination agent. The brominated indane is excellent in flame-resistance, has a high thermal decomposition temperature and never generates brominated dioxine and/or brominated dibenzofuran when burning at a specific temperature. Therefore, the compound is suitably used for imparting flame-resistance to a variety of thermoplastic and thermosetting resins.

12 Claims, 2 Drawing Sheets

BROMINATED 1,3-DIMETHYL-3-PHENYL-1-(2-METHYL-2-PHENYLPROPYL)-INDANE AND METHOD FOR PREPARING THE SAME

BACKGROUND OF THE INVENTION

1. Field of the Invention

The present invention relates to a brominated 1,3-dimethyl-3-phenyl-1-(2-methyl-2-phenylpropyl) indane and a method for preparing the compound.

2. Description of the Prior Art

There have conventionally been used bromide compounds having high heat resistance and excellent in a variety of characteristic properties such as electrical insulating properties in order to impart flame resistance to various kinds of thermoplastic resins and thermosetting resins. In particular, in the field requiring the use of an externally added type compound having high heat resistance, there have been used brominated atom-containing aromatic compounds, i.e., aromatic compounds each having bromine atom(s) directly linked to the aromatic ring(s), such as decabromodiphenyl ether, tetrabromobisphenol A epoxy oligomer, tetrabromobisphenol A polycarbonate oligomer, brominated polystyrene and ethylene bistetrabromophthalimide. In addition, there have newly been developed brominated atom-containing compounds such as 1,1,3-trimethyl-3-phenyl indane as disclosed in Japanese Un-Examined Patent Publication (hereinafter referred to as "J.P. KOKAI") No. Hei 6-122637.

The externaly added flame-resistant agents should satisfy such requirements that they must have a high decomposition temperature and that they must have good fabrication properties, i.e., they must have a melting point favorable for uniformly kneading them with a base resin. The foregoing flame-resistant agents such as decabromodiphenyl ether, tetrabromobisphenol A epoxy oligomer, tetrabromobisphenol A polycarbonate oligomer, brominated polystyrene and ethylene bistetrabromophthalimide each has a thermal decomposition temperature of not less than 300° C., but decabromodiphenyl ether is the only example of compounds whose bromine content is not less than 70%. However, decabromodiphenyl ether suffers from a problem in that the molding temperature should be raised up to a level of not less than 306° C. to obtain a uniform blend with a base resin since it has a high melting point on the order of 306° C. For this reason, there has usually been adopted a method in which the compound in the particulate form is dispersed in a base resin as uniform as possible. Moreover, polybromobiphenyl ethers have given rise to public discussion, because there has been reported that they may generate brominated dioxine and/or brominated dibenzofuran when burning them at a specific temperature (Environ. Sci. Technol., 1986,20, 4, pp. 404–408). In addition, octabromo-1,1,3-trimethyl-3-phenylindane has a slightly low thermal decomposition temperature on the order of 296° C. and accordingly, there has been desired for the development of a flame-resistant agent having a higher thermal decomposition temperature.

SUMMARY OF THE INVENTION

Accordingly, an object of the present invention is to provide a brominated 1,3-dimethyl-3-phenyl-1-(2-methyl-2-phenylpropyl) indane which is excellent in flame-resistance, has a high thermal decomposition temperature and is excellent in fabrication properties.

Another object of the present invention is to provide a brominated 1,3-dimethyl-3-phenyl-1-(2-methyl-2-phenylpropyl) indane which is particularly excellent in fabrication properties, in addition to the foregoing characteristic properties.

A further object of the present invention is to provide a brominated 1,3-dimethyl-3-phenyl-1-(2-methyl-2-phenylpropyl) indane which is particularly excellent in flame-resistance and has a higher thermal decomposition temperature, in addition to the foregoing characteristic properties.

A still further object of the present invention is to provide a method for preparing the foregoing compound which is excellent in flame-resistance, has a high thermal decomposition temperature and is excellent in fabrication properties.

A further object of the present invention is to provide a method for preparing the foregoing compound, which permits the production thereof in a short time and in a high yield.

A still object of the present invention is to provide a method for preparing the foregoing compound, which permits the production thereof in a short time and in a high yield and at a low cost.

A still further object of the present invention is to provide a method for preparing the foregoing compound, which permits the production thereof in a much shorter time, and in a high yield.

According to an aspect of the present invention, there is provided a brominated 1,3-dimethyl-3-phenyl-1-(2-methyl-2-phenylpropyl) indane represented by the following general formula (I):

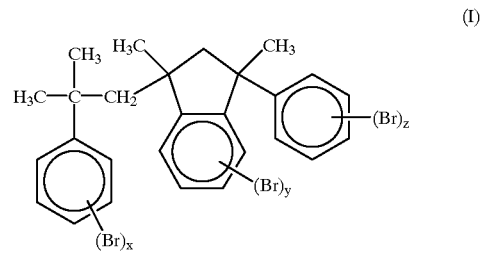

(wherein x and z each independently represents an integer ranging from 0 to 5, y represents an integer ranging from 0 to 4, provided that $x+y+z \geq 1$).

According to another aspect of the present invention, there is provided a brominated 1,3-dimethyl-3-phenyl-1-(2-methyl-2-phenylpropyl) indane represented by the foregoing general formula (I) wherein $x+y+z \geq 3$.

According to a further aspect of the present invention, there is provided a brominated 1,3-dimethyl-3-phenyl-1-(2-methyl-2-phenylpropyl) indane represented by the foregoing general formula (I) wherein $x+y+z \geq 11$.

According to a still further aspect of the present invention, there is provided a method for preparing a brominated 1,3-dimethyl-3-phenyl-1-(2-methyl-2-phenylpropyl) indane represented by the foregoing general formula (I), which comprises the step of reacting 1,3-dimethyl-3-phenyl-1-(2-methyl-2-phenylpropyl) indane with a bromination agent.

The method of the present invention preferably carried out at a bromination reaction temperature ranging from 0 to 70° C., during the reaction of 1,3-dimethyl-3-phenyl-1-(2-methyl-2-phenylpropyl) indane with a bromination agent and in a preferred embodiment, the bromination agent is bromine.

According to a further aspect of the present invention, there is provided a method for preparing a brominated 1,3-dimethyl-3-phenyl-1-(2-methyl-2-phenylpropyl) indane represented by the foregoing general formula (I), which comprises the step of reacting 1,3-dimethyl-3-phenyl-1-(2-methyl-2-phenylpropyl) indane with a bromination agent in the presence of a catalyst in an organic solvent.

DESCRIPTION OF THE PREFERRED EMBODIMENTS

Figure 1:
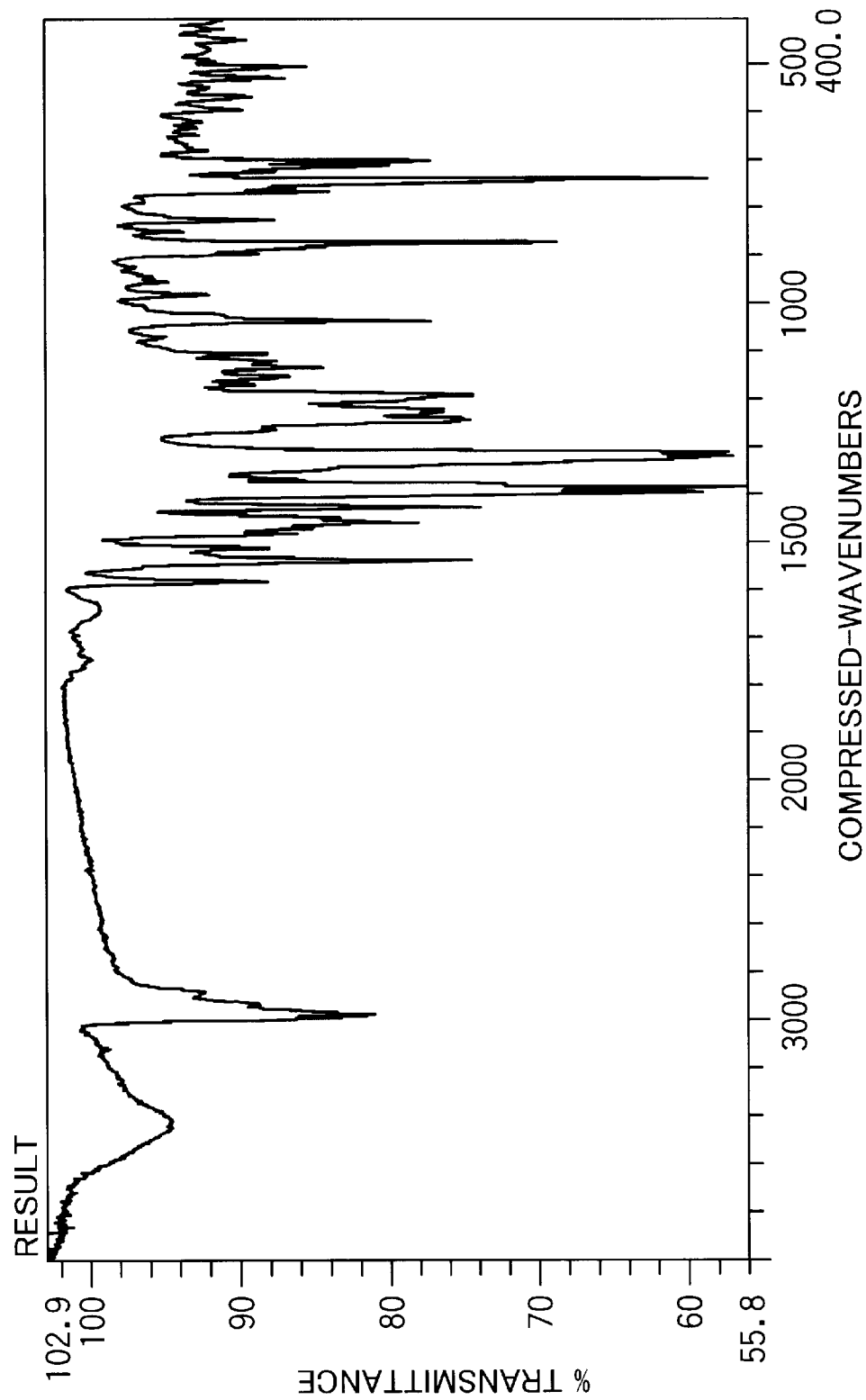
FIG. 1 is the IR spectrum observed for the undecabromo 1,3-dimethyl-3-phenyl-1-(2-methyl-2-phenylpropyl)indane prepared in Example 1.

The brominated 1,3-dimethyl-3-phenyl-1-(2-methyl-2-phenylpropyl) indane (hereinafter referred to as "MPIB") according to the present invention is a compound represented by the foregoing general formula (I). In the general fromula (I), x and z each independently represents an integer ranging from 0 to 5, y represents an integer ranging from 0 to 4, provided that $x+y+z \geq 1$. Preferred compounds are those represented by Formula (I) wherein $x+y+z \geq 3$, more preferably $x+y+z \geq 11$. The higher the value of x+y+z, i.e., the higher the bromine atom content, the higher the flame-resistant characteristics of a flame-resistant compound. However, the MPIB of the present invention is sometimes used in combination with other flame-resistant agents or flame-retardant auxiliary agents and the value of x+y+z may be small when the compound may have a plasticizing effect although the bromine content thereof is low.

The method of the present invention is characterized by reacting (A) 1,3-dimethyl-3-phenyl-1-(2-methyl-2-phenylpropyl) indane (hereinafter referred to as "MPI") with (B) a bromination agent.

MPI can be prepared by converting α-methylstyrene into its trimer. Typical conditions for synthesizing the same are disclosed in Japanese Examined Patent Publication (hereinafter referred to as "J.P. KOKOKU") No. Sho 57-10851, but the reaction carried out under these conditions provides a mixture of linear and cyclic, dimeric to tetrameric compounds. MPI can be obtained by purifying the mixture through the vacuum distillation.

Bromine, bromates, hydrogen bromide or the like may be used as the bromination agents, with bromine being preferred because it is not expensive. The blending ratio of MPI to the bromination agent is determined depending on the desired bromination rate, but the amount of the bromination agent is preferably slightly greater than the stoichiometric amount thereof.

The bromination reaction may be carried out according to a method in which the bromination agent is dropwise added to MPI or a method wherein MPI is dropwise added to the bromination agent, but preferred is the latter method in order to synthesize MPIB having a higher bromine atom content.

The bromination reaction temperature varies depending on the kind of the bromination agent selected, but it preferably ranges from 0 to 70° C. This is because if the reaction temperature is lower than 0° C., the reaction may require a long time period, while if it exceeds 70° C., the main chain of MPI may undergo cleavage due to a side-reaction.

The foregoing bromination reaction may be carried out in an organic solvent and the organic solvent usable herein is not restricted to any specific one so far as it never inhibits the reaction, but examples thereof preferably used include halogenated aliphatic hydrocarbons such as dibromomethane, dibromoethane, tribromoethane, tetrabromoethane, methylene chloride, chloroform, carbon tetrachloride, dichloroethane, trichloroethane and tetrachloroethane, with dibromomethane and dibromoethane being more preferably used.

The foregoing bromination reaction may be carried out in the presence of a catalyst and the catalyst usable herein is preferably a metal catalyst or a Lewis acid catalyst, such as Fe, $AlCl_3$, $AlBr_3$, $FeCl_3$, $FeBr_3$, $BF_3$, $BF_3$ derivatives, $BCl_3$, $BBr_3$, $SbCl_3$, $SbBr_3$, $SnCl_4$, $SnBr_4$, $ZrCl_4$ and $ZrBr_4$, with Fe and $AlCl_3$ being preferred among others. The amount of the catalyst preferably ranges from 1 to 10 parts by weight and more preferably 3 to 7 parts by weight per 100 parts by weight of MPI. This is because if the amount of the catalyst used is less than 1 part by weight, the rate of the bromination reaction may considerably be reduced, while if it exceeds 10 parts by weight, the yield of the desired bromide would be reduced because of side-reactions.

The bromination reaction time is preferably established to the range of from 3 to 24 hours, more preferably 4 to 12 hours and most preferably 6 to 9 hours. If the reaction time is less than 3 hours, the progress of the bromination reaction may be insufficient, while if it exceeds 24 hours, the reaction is liable to be accompanied by side-reactions such as the cleavage of the main chain of MPI.

The pressure of the bromination reaction system is not particularly limited and it is sufficient to carry out the reaction under ordinary pressure.

Furthermore, there s no obstacle if MPIB included a brominated 1,1-dimethyl-3-phenyl-3-(2-methyl-2-phenylpropyl) indane as the side-reaction product when MPIB is prepared.

The present invention will hereinafter be described in more detail with reference to the following working Examples, but the present invention is not restricted to these specific Examples.

EXAMPLE 1

Synthesis of 1,3-Dimethyl-3-Phenyl-1-(2-Methyl-2-Phenylpropyl) Indane (MPI)

To a four-necked 2000 ml-volume flask equipped with a stirring machine, a dropping funnel, a Dimroth condenser and a thermometer, there was added a solution of 300.4 g of α-methylstyrene in 1200 g of toluene, followed by setting the temperature thereof to 0° C. by dipping the flask in ice-water and gradual dropwise addition of 300 ml of a toluene solution containing a catalyst, i.e., 1.02 g $AlCl_3$-2.5 ml $CH_3NO_3$ to the contents of the flask with stirring. The reaction solution at the completion of the reaction-was colored pale yellow. After the completion of the reaction, water was gently dropwise added to the reaction system to thus decompose the catalyst. Then the organic phase was washed with water, dried and concentrated. Further the organic phase was subjected to vacuum distillation under a degree of vacuum of 670 Pa and at a temperature ranging from 218 to 221° C. to give 140.0 g of 1,3-dimethyl-3-phenyl-1-(2-methyl-2-phenylpropyl) indane (MPI).

Synthesis of Brominated 1,3-Dimethyl-3-Phenyl-1-(2-Methyl-2-Phenylpropyl) Indane (MPIB)

To a three-necked 1000 ml-volume flask equipped with a stirring machine, a dropping funnel, a Dimroth condenser and a thermometer, there were added 95 ml (1840 m mole)

of bromine, 125 ml of dibromoethane as a solvent and 1.67 g (12.52 m mole) of $AlCl_3$ as a catalyst. On the other hand, a solution of 35.45 g (100 m mole) of 1,3-dimethyl-3-phenyl-1-(2-methyl-2-phenylpropyl) indane (MPI) dissolved in 125 ml of dibromoethane was introduced into the dropping funnel. The temperature of the contents of the flask was set to 35° C. using an oil bath and the MPI solution was dropwise added thereto over 1.33 minute. The reaction system was continued stirring for 250 minutes after the initiation of the dropwise addition, thereafter the temperature of the system was raised up to 60° C. over 10 minutes followed by continuous stirring over 240 minutes. After the whole system was cooled to room temperature, the reaction was terminated by addition of water. Further a 10% by weight aqueous solution of sodium hydrogen sulfite to remove the residual bromine, followed by washing with water, removal of the solvent from the mixture of precipitates and the solvent through filtration, washing with acetone and drying to give 28.7 g (yield 23.5%) of a pale yellow and powdery product A.

Product A was analyzed by the elemental analysis and the results were found to be as follows: C, 26.24%; H, 1.32%; Br, 72.12%. Theoretically, the undecabromo-substituted product comprises carbon atom of 26.53%, hydrogen atom of 1.57% and bromine atom of 71.90% and therefore, the foregoing results are in good agreement with the latter. In addition, Product A was analyzed by HPLC and it was found that a principal peak was observed at a retention time of 25.5 minutes. In this connection, the HPLC was performed using a column, TSK-G1000HHR, available from Tosoh Corporation, a hexane/toluene (volume ratio: 7/3~5/5) mixed solvent as an eluent and a UV detector (measured at a wavelength of 282 nm), at a flow rate of 1.0 ml/min.

Figure 2:
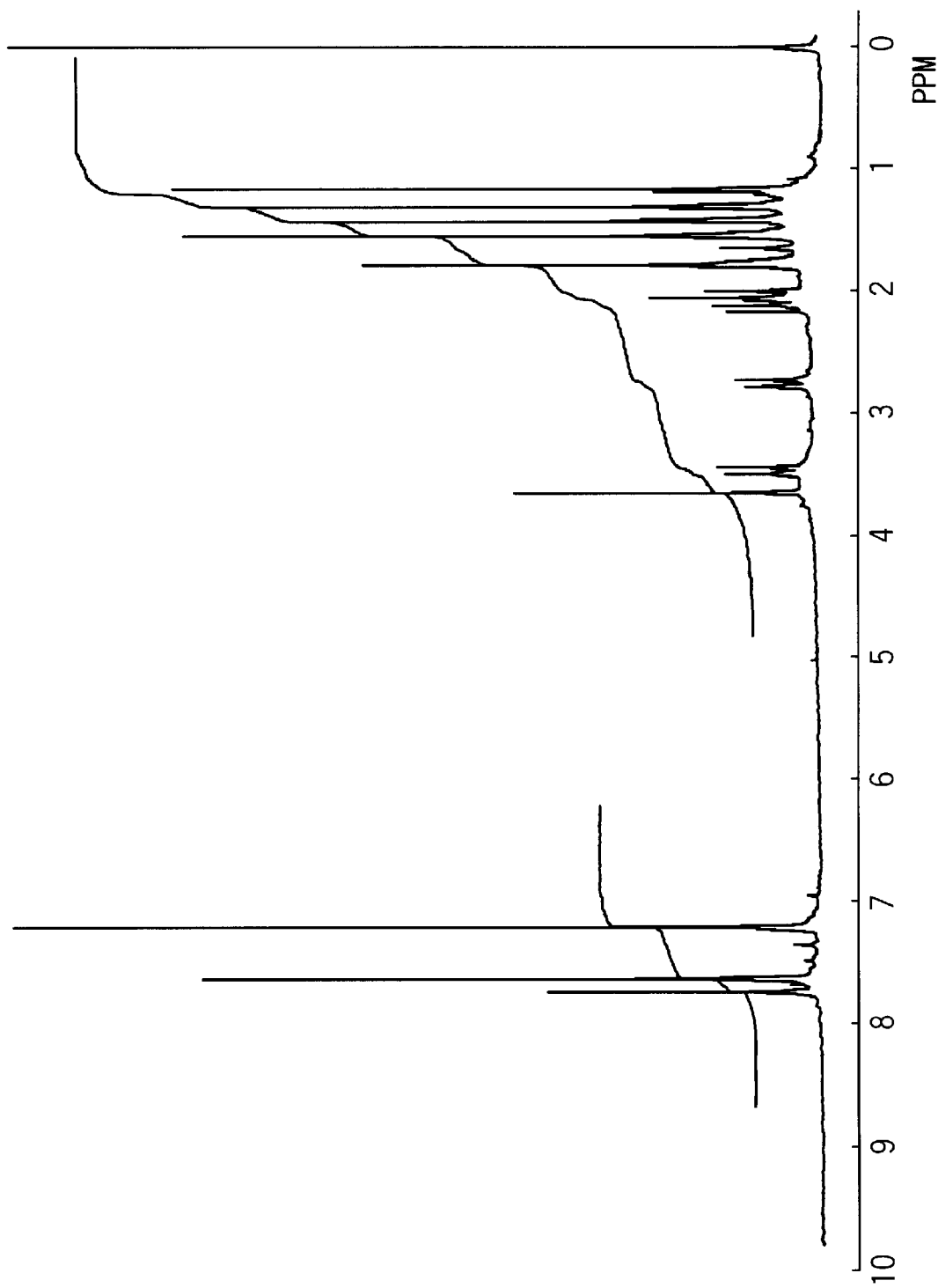
FIG. 2 is the proton NMR spectral chart observed for the undecabromo 1,3-dimethyl-3-phenyl-1-(2-methyl-2-phenylpropyl)indane prepared in Example 1.

Product A was analyzed by IR and proton NMR spectroscopic measurements. The results are shown in FIGS. 1 and 2, respectively.

In the IR spectrometry (KBr method), there were observed absorption bands at 1030 $cm^{-1}$, 870 $cm^{-1}$ and 739 $cm^{-1}$ which could be assigned to the linkage between a carbon atom on the aromatic ring and a bromine atom.

In addition, there were observed 4 singlet absorption bands at 1.13 ppm, 1.27 ppm, 1.39 ppm and 1.74 ppm ascribed to the presence of four methyl groups, respectively; two quartet absorption bands at 2.03 ppm and 3.08 ppm ascribed to the presence of two methylene groups; and two absorption bands at 7.76 ppm and 7.72 ppm ascribed to three hydrogen atoms on the aromatic ring, in the proton NMR spectroscopic analysis (solvent: $CDCl_3$). The absorption bands to be ascribed to methylene groups are splitted into quartet bands because of the presence of two optically active carbon atoms in the molecule. In this respect, the absorption bands observed at 1.51 ppm, 3.60 ppm and 7.17 ppm can be ascribed to water, dibromoethane and chloroform as the residual solvents, respectively.

Moreover, Product A was subjected to the mass spectroscopic analysis. As a result, there were observed fragment ion peaks at m/z values of 355 and 852. The fragment observed at m/z of 355 can be ascribed to a tribromo-substituted product which is formed through the cleavage at the site on dimethylbenzyl group, while that observed at m/z of 852 can be ascribed to an octabromo-substituted product formed through the cleavage at the site on the indane ring.

These results clearly indicate that Product A mainly comprises a derivative of MPI whose aromatic rings carry 11 bromine atoms in total.

The melting point of Product A was determined by DSC (differential scanning calorimeter) and found to be 295° C.

In addition, the pyrolytic properties of Product A were also determined by TGA (thermogravimetric analyzer) and as a result, the initiation temperature of thermo-degradation thereof was found to be 316° C. This indicates that Product A has high heat-resistance.

EXAMPLE 2

The same procedures used in Example 1 were repeated except that 0.70 g (12.50 mM) of iron was substituted for 1.67 g (12.52 mM) of $AlCl_3$ as a catalyst to obtain a product B.

Product B was subjected to the mass spectroscopic analysis. As a result, there were observed fragment ion peaks at m/z values of 355 and 772. The fragment observed at m/z of 355 can be assigned to a tribromo-substituted product which is formed through the cleavage at the site on dimethylbenzyl group, while that observed at m/z of 772 can be assigned to a heptabromo-substituted product formed through the cleavage at the site on the indane ring. These results clearly indicate that Product B mainly comprises a derivative of MPI whose aromatic rings carry 10 bromine atoms in total.

EXAMPLE 3

To a three-necked 200 ml flask equipped with a stirring machine, a dropping funnel, a Dimroth condenser and a thermometer, there were added 10.6 g (30 m mole) of 1,3-dimethyl-3-phenyl-1-(2-methyl-2-phenylpropyl) indane (MPI), 40 ml of dibromoethane as a solvent and 0.33 g (2.5 m mole) of $AlCl_3$ as a catalyst. On the other hand, a solution of 20.0 g (125 m mole) of bromine dissolved in 15 ml of dibromoethane was introduced into the dropping funnel. The temperature of the content of the flask was set to 22° C. and the bromine solution was dropwise added to the MPI solution over 20 minutes. The reaction system was continued stirring for 70 minutes after the initiation of the dropwise addition. Thereafter, the reaction was terminated by addition of water. Further a 10% by weight aqueous solution of sodium hydrogen sulfite to remove the residual bromine, followed by washing with water, removal of the solvent through distillation. The resulting reaction product was a brown and highly viscous liquid. The highly viscous liquid was purified by treating it through silica gel dry chromatography (Wako Gel C200; eluent: 500/10 hexane/toluene mixed solvent) followed by distillation of the solvent to give 6.1 g (yield 33%) of a product C as a yellow solid.

Product C was analyzed by the elemental analysis and the results were found to be as follows: C, 52.64%; H, 4.31%; Br, 43.37%. Theoretically, the 3.3 bromo-substituted product comprises carbon atom of 52.41%, hydrogen atom of 4.34% and bromine atom of 43.37% and therefore, the foregoing results are in good agreement with the latter.

Moreover, Product C was subjected to the mass spectroscopic analysis and there were observed fragment ion peaks at m/z values of 197, 379 and 457. The fragment observed at m/z of 197 can be ascribed to a monobromo-substituted product which is formed through the cleavage at the site on dimethylbenzyl group, the fragment observed at m/z of 379 can be ascribed to a dibromo-substituted product which is formed through the cleavage at the site on the indane ring and that observed at m/z of 457 can be ascribed to a tribromo-substituted product formed through the cleavage at the site on the indane ring. These results clearly indicate that Product C mainly comprises a derivative of MPI whose aromatic rings carry 3 or 4 bromine atoms in total.

EXAMPLE 4

To a three-necked 200 ml flask equipped with a stirring machine, a dropping funnel, a Dimroth condenser and a thermometer, there were added 10.6 g (30 m mole) of 1,3-dimethyl-3-phenyl-1-(2-methyl-2-phenylpropyl) indane (MPI), 40 ml of dibromoethane as a solvent and 0.66 g (5 m mole) of AlCl₃ as a catalyst. On the other hand, a solution of 50.4 g (315 m mole) of bromine dissolved in 15 ml of dibromoethane was introduced into the dropping funnel. The temperature of the content of the flask was set to 47~50° C. and the bromine solution was dropwise added to the MPI solution over 40 minutes. The reaction system was continued stirring for 240 minutes after the initiation of the dropwise addition. Thereafter, the reaction was terminated by addition of water. Further a 10% by weight aqueous solution of sodium hydrogen sulfite to remove the residual bromine, followed by washing with water and removal of the solvent through distillation. The resulting reaction product was a brown and highly viscous liquid. The highly viscous liquid was purified by treating it through silica gel dry chromatography (Wako Gel C200; eluent: 500/10 hexane/toluene mixed solvent) followed by distillation of the solvent to give 4.9 g (yield 16%) of a product D as pale brownish powder.

Product D was analyzed by the elemental analysis and the results were found to be as follows: C, 32.43%; H, 1.88%; Br, 64.99%. Theoretically, the octabromo-substituted product comprises carbon atom of 32.77%, hydrogen atom of 2.24% and bromine atom of 64.99% and therefore, the foregoing results are in good agreement with the latter.

Moreover, Product D was subjected to the mass spectroscopic analysis and there were observed fragment ion peaks at m/z values of 277, 355, 537, 615 and 695. The fragment observed at m/z of 277 can be ascribed to a dibromo-substituted product which is formed through the cleavage at the site on the dimethylbenzyl group, the fragment observed at m/z of 355 can be ascribed to a tribromo-substituted product which is formed through the cleavage at the site on the benzyl group, the fragment observed at m/z of 537 can be ascribed to a tetrabromo-substituted product which is formed through the cleavage at the site on the indane ring, the fragment observed at m/z of 615 can be ascribed to a pentabromo-substituted product which is formed through the cleavage at the site on the indane ring and that observed at m/z of 695 can be ascribed to a hexabromo-substituted product formed through the cleavage at the site on the indane ring. These results clearly indicate that Product D mainly comprises a derivative of MPI whose aromatic rings carry 7 or 8 bromine atoms in total.

As has been discussed above in detail, the brominated indane represented by Formula (I) according to the present invention is excellent in flame-resistance, has a high thermal decomposition temperature and never generates brominated dioxine and/or brominated dibenzofuran when burning at a specific temperature. In addition, the compounds of the present invention according to preferred embodiments (in Formula (I), $x+y+z \geqq 3$ or 11) are particularly excellent in fabrication properties because of a melting point favorable for uniform kneading thereof with a base resin or particularly excellent in flame-resistance because of a high bromine content. Therefore, they can be suitably used for imparting flame-resistance to a variety of thermoplastic and thermosetting resins.

Moreover, the method of the present invention permits the production of the foregoing compounds within a short period of time, at a high yield and at a low cost.

What is claimed is:

1. A brominated 1,3-dimethyl-3-phenyl-1-(2-methyl-2-phenylpropyl) indane represented by the following general formula (I):

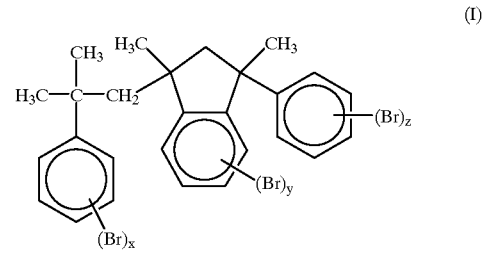

(wherein x and z each independently represents an integer ranging from 0 to 5, y represents an integer ranging from 0 to 4, provided that $x+y+z \geqq 1$).

2. The brominated indane of claim 1 wherein in Formula (I), $x+y+z \geqq 3$.

3. The brominated indane compound of claim 1 wherein in Formula (I), $x+y+z \geqq 11$.

4. A method for preparing a brominated 1,3-dimethyl-3-phenyl-1-(2-methyl-2-phenylpropyl) indane represented by the foregoing general formula (I), comprising the step of reacting 1,3-dimethyl-3-phenyl-1-(2-methyl-2-phenylpropyl) indane with a bromination agent.

5. The method of claim 4 wherein the bromination reaction is carried out at a temperature ranging from 0 to 70° C.

6. The method of claim 4 wherein the bromination agent is bromine.

7. The method of claim 4 wherein the bromination reaction is carried out in the presence of a catalyst in an organic solvent.

8. The method of claim 7 wherein the catalyst is Fe or AlCl₃.

9. The method of claim 7 wherein the amount of the catalyst ranges from 1 to 10 parts by weight per 100 parts by weight of 1,3-dimethyl-3-phenyl-1-(2-methyl-2-phenylpropyl) indane.

10. The method of claim 4 wherein the bromination reaction is carried out by dropwise addition of 1,3-dimethyl-3-phenyl-1-(2-methyl-2-phenylpropyl) indane to the bromination agent.

11. The method of claim 4 wherein the amount of the bromination agent is slightly greater than the stoichiometric amount thereof.

12. The method of claim 4 wherein the reaction time ranges from 3 to 24 hours.

* * * * *